(12) United States Patent
Buck

(10) Patent No.: US 6,517,822 B1
(45) Date of Patent: *Feb. 11, 2003

(54) FORMULATIONS AND METHODS FOR STRAIGHTENING HAIR

(76) Inventor: Carol J. Buck, 30 Brooks Bend, Princeton, NJ (US) 08540

( * ) Notice: Subject to any disclaimer, the term of this patent is extended or adjusted under 35 U.S.C. 154(b) by 0 days.

This patent is subject to a terminal disclaimer.

(21) Appl. No.: 09/514,049

(22) Filed: Feb. 25, 2000

Related U.S. Application Data

(63) Continuation-in-part of application No. 09/023,449, filed on Feb. 13, 1998.

(51) Int. Cl.[7] .................... A61K 7/09; A61K 31/19
(52) U.S. Cl. ................ 424/70.2; 424/70.1; 514/557
(58) Field of Search ................ 424/70.1, 70.2; 426/17; 514/557

(56) References Cited

U.S. PATENT DOCUMENTS

| | | | |
|---|---|---|---|
| 3,654,936 A | | 4/1972 | Wajaroff |
| 4,030,512 A | | 6/1977 | Papantoniou et al. |
| 4,296,130 A | * | 10/1981 | Herschler .................... 424/337 |
| 4,313,960 A | * | 2/1982 | Campagne .................... 426/17 |
| 4,363,815 A | | 12/1982 | Yu et al. |
| 4,424,820 A | | 1/1984 | Cannell et al. |
| 4,859,459 A | | 8/1989 | Greiche et al. |
| 4,906,461 A | * | 3/1990 | Chambers .................... 424/74 |
| 5,091,171 A | | 2/1992 | Yu et al. |
| 5,635,168 A | * | 6/1997 | Burns et al. ................ 424/70.4 |
| 5,690,956 A | * | 11/1997 | Lau ............................ 424/450 |
| 5,989,534 A | * | 11/1999 | Samain .................... 424/70.51 |
| 6,146,619 A | * | 11/2000 | Cortekar et al. ........... 424/70.1 |
| 6,231,840 B1 | * | 5/2001 | Buck ........................... 424/61 |

FOREIGN PATENT DOCUMENTS

JP       631053511 A  *  4/1985

OTHER PUBLICATIONS

Heinz Apple Cider Vinegar product label.*
Morita et al. (1986) JP 361063611 A, Abstract.*

* cited by examiner

Primary Examiner—Russell Travers
Assistant Examiner—Gina C Yu
(74) Attorney, Agent, or Firm—Mathews, Collins, Shepherd & McKay, P.A.

(57) ABSTRACT

A formulation is described for straightening hair comprising alkanoic acids and a diluent, wherein the diluent is advantageously present at greater than 5% by volume, and more preferably greater than 20% by volume. The inventive formulation is acidic and does not use an effective amount of an alkaline hair-straightening agent to perform the hair straightening function. Instead, the step of hair straightening is accomplished by applying the non-alkaline formulation to the hair and then either leaving the formulation in the hair without rinsing or rinsing the formulation out of the hair followed by optional shampooing and/or conditioning. Consequently, a safe and surprisingly effective solution is provided for hair-straightening including hair-straightening maintenance, relaxation of curl, and reduction of frizziness (e.g., in humid weather).

10 Claims, 9 Drawing Sheets

FORMULATIONS AND METHODS FOR STRAIGHTENING HAIR

RELATED APPLICATIONS

This application is a continuation-in-part of U.S. patent application Ser. No. 09/023,449, filed Feb. 13, 1998 and claims the benefit of the priority date thereof.

FIELD OF THE INETION

The invention relates to formulations and methods for straightening or relaxing the curl of hair, particularly naturally kinky and curly hair.

BACKGROUND OF THE INVETION

Hair generally can be divided into four categories: (i) straight, (ii) wavy, (iii) curly, and (iv) kinky. The human hair shaft is comprised of three concentric layers identified as the cuticle (a thin, outer-most shell); the cortex (the main body of the hair); and the medulla (a thin, central core). The cuticle and cortex are responsible for the hair shaft's mechanical properties, that is, its tendency to curl (in some hair the medulla is absent). The condition of the cuticle is responsible for the outward appearance of the hair, particularly feel and shine. Straight hair resembles a rod with a circular diameter; wavy hair shafts are compressed into an oval diameter; curly shafts are further compressed into an elongated ellipse; and kinky hair shafts are flatter still. Hair shaft configurations can be represented as follows:

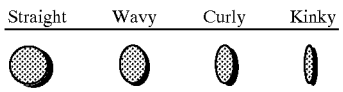

Many people with naturally kinky, curly, or even wavy hair often desire to straighten their hair. There are a number of hair straightening compositions and methods available today, but these involve use of harsh straightening agents such as alkaline or sulfite-based chemicals. To permanently alter the natural curl of human hair, a number of types of bonds within the hair are cleaved, including salt bridges and disulfide bonds. Human hair is composed of cross-linked, α-helix protein, primarily keratin. Keratin is a complex of polypeptide chains of high molecular weight. The hair shaft will maintain its outward shape by ionic bonding or salt bridges (disulfide or cystine bridges) which pair various amino acids found in the hair. Current straightening methods break disulfide bonds into free sulfhydryls and then re-establish new disulfide bonds in the desired configuration by reduction/oxidation of the hair shaft using various chemicals.

Most permanent straightening products marketed today use one of five types of chemicals: (1) thioglycolate-based products, (2) sulfite-bisulfite products, (3) sodium hydroxide (alkali) products, (4) lithium hydroxide, and (5) acetamide (formulated as a between-shampoos, aerosol styling aid). See, e.g. AMA BOOK OF SKIN AND HAIR CARE, Schoen, LA, Ed., American Medical Association, (JB Lippincott Co., New York 1976), which is incorporated herein, at p. 116–119. In all these cases excepting acetamide, the chemical agent is applied to clean, damp hair that has been pulled straight by combing action. After a carefully-measured period of time, the disulfide bonds are broken, the solution is rinsed off, and a second solution (often hydrogen peroxide or other oxidizing agent) is applied to neutralize the reaction. These products produce varying levels of effectiveness in hair straightening; however, there are drawbacks to using them in terms of safety, toxicity, risk of damaging the hair, and protection of the skin and scalp.

For example, thioglycolate straighteners produce reversible changes in the chemical disulfide bonds of hair by generating free oxygen radicals for 10 to 20 minutes. Concern about the teratogenicity of thioglycolate has recently caused the United States Department of Health and Human Services to post notice of a need to review their safety for human use. Bisulfite straighteners produce reversible bond changes, and are milder on skin than thioglycolate straighteners. However, bisulfite straighteners still present a risk of hair and skin damage, and they are typically used in combination with alkaline agents which can irritate and burn the skin and scalp. In the straightening procedure, bisulfite lotion is applied to clean, damp hair, which is covered in plastic for a period of time, then combed straight, rinsed, treated with an alkaline stabilizer, and conditioned.

Like other known methods, alkali lotions cannot be used on irritated or injured scalps. Also, the harshness of alkali lotions presents the risk of skin irritations or burns on a healthy scalp. As new hair grows in, it alone should be exposed to the chemical straighteners, an often delicate and difficult procedure that avoids lotion contact with both the scalp and the previously treated hair. In this method, sodium hydroxide lotion is applied to the hair and smoothed flat with finger pressure. A 'normalizer' pre-shampoo rinse is then applied followed by a water rinse. The hair is then shampooed twice, conditioned and administered a setting/styling/wrapping lotion prior to styling and drying.

Typically, to be effective as a straightening agent, the alkali hair straighteners include use of about 1.8 to 4 weight % of strong bases, such as sodium hydroxide, potassium hydroxide, or lithium hydroxide. Use of alkali agents at these concentrations result in compositions having pH values of above 9pH, and more often above 12 pH. For example, a hair relaxer referred to as CLEARGEL 862™ uses a 50% solution with 3.5 wt. % sodium hydroxide which produces a composition having a pH of 12.5 to 12.7 at 25° C. Use of alkaline agents at such concentrations presents a safety risk and also complicates the process of hair straightening, as various steps need to be made to protect the scalp and administer the lotion. As an illustration, U.S. Pat. No. 4,592,908 to Wajaroff et al. discloses a protective cream that is adapted to be applied to the scalp before a strongly alkaline hair-straightening agent is used. Wajaroff's cream comprises VASELINE® and organic acids, containing less than 1% water, which is applied to the scalp, but not the hair. A strongly alkaline hair-straightening agent is then applied to the hair. According to the Wajaroff method, the cream placed on the scalp will neutralize the alkaline agents that may reach the scalp, thus protecting the scalp. The Wajaroff method, however, uses strongly alkaline agents, and additionally, it requires extra steps in applying the protective gel to the scalp and then removing that gel after the hair straightening steps have been performed.

The "no lye" method uses lithium hydroxide, also a human toxin, in combination with other ingredients as the relaxing agent. The user is also cautioned against skin and scalp burns, possible hair loss, and eye injury. The product is contraindicated for persons with damaged or chemically-treated hair and irritated scalp. Acetamide ($CH_3CONH_2$) is an organic, crystal compound in the urea and guanine series which has recently been formulated into a cosmetic spray-on, straightener styling aid for use between shampoos.

Acetamide is a known irritant to the eyes, nose, and throat and has shown low-to-moderate acute toxicity from oral exposure, including liver tumors, in animal studies.

Other methods of breaking disulfide bonds in hair employ high-heat appliances. In this method heat combs set at 300° F. are pulled quickly through long hair, which instantly breaks disulfide bonds leaving the hair straight. This process can result in damaging hair permanently if the temperature and combing speed are not carefully managed.

U.S. Pat. No. 3,654,936 to Wajaroff describes the use of a keratin softener for straightening hair. In this method hair is treated with a reducing agent then straightened by the action of a "keratin softener" combined with swelling or penetration-promoting agents, while being straightened mechanically prior to the application of a fixation agent.

Other straightening methods include the use of humectants such as fatty acid lactylates and fatty acid glycolates to improve the hair's texture (see U.S. Pat. No. 4,424,820, "*Hair Straightening Compositions Containing Fatty Acid Lactylates and Glycolates and their Method of Use,*" issued to Cannell, D. et al. and assigned to Redken Laboratories, which is incorporated herein), and the use of dipropylene glycol monomethyl ether as a swelling and penetrating agent. (See U.S. Pat. No. 4,859,459, "*Method of Shaping Human Hair Using Dipropylene Glycol Monomethyl Ether,*" Greiche, J., et al., assigned to Wella Aktiengesellschaft, Germany, also incorporated herein.)

Accordingly, the current methods of hair straightening remain dangerous to the skin, eyes, and hair. In some cases, direct contact between the skin and the straightening agent can result in second- and third-degree chemical burns or even hair loss. None of the known methods are recommended if the scalp or skin is sensitive, scaly, scratched, sore or tender. Unsatisfactory and sometimes harmful results occur if the directions are not carefully followed. As may be appreciated, there is a need for a hair-straightening composition and method that avoids the use of harmful chemicals and irritants that have been used in previous compositions. There further remains a need for a hair straightening agent that provides the consumer with a greater choice of options and products that may be safely used at home.

SUMMARY OF THE INVENTION

Applicant has discovered a formulation for straightening hair that avoids the dangers of the alkaline and other harsh ingredients of prior art compositions. The present invention relates to formulations for straightening hair comprising alkanoic acids, combined with water, optionally in combination with other suitable diluents. The inventive formulation is acidic, not alkaline, and the acids suitable for use in the inventive formulations preferably are selected from acetic and propanoic acids. The invention does not use an alkaline hair-straightening agent to perform the hair straightening function. Instead, the step of hair straightening is accomplished by applying the non-alkaline, alkanoic acid and water formulation to the hair and then either leaving the formulation in the hair without rinsing, or shampooing the formulation out of the hair followed by optional conditioning. The formulation is also effective for hair-straightening maintenance, relaxation of curl, and reduction of frizziness of hair produced from humid weather.

BRIEF DESCRIPTION OF THE DRAWINGS

For a better understanding of the invention, exemplary embodiments are described below, considered together with the accompanying figures, in which.

DETAILED DESCRIPTION OF THE INVENTION

Figure 1A:
FIGS. 1A and 1B are photographs showing the condition of a subject's hair before and after treatment, respectively, with one embodiment of the inventive formulations using 18% acetic acid and greater than 50% water as a diluent.

The invention relates to formulations and methods for safely straightening (relaxing) hair, including naturally kinky, curly or wavy hair. The inventive formulation comprises a solution containing alkanoic acid and a diluent. The formulation is safe and does not present a risk of irritating or burning the skin or scalp. No protective creams, need to be applied to protect the skin or scalp in using the formulation. Advantageously, the formulation contains greater than 5% (w/w) alkanoic acid and greater than 5% (w/w) of the diluent, more preferably greater than 20% of the diluent, and even more preferably greater than 50% of the diluent. With regard to the concentration of the alkanoic acid, maximum hair-straightening results are achieved when the formulation contains in the range of about 30–70% (w/w) of the alkanoic acid. A formulation having 95% acid retains some effectiveness, but a concentration having 99% acid has been found to be ineffective. Formulations having greater than 30% alkanoic acid are not recommended, however, in seeking to maintain maximum safety benefits of the invention. When less than 30% alkanoic acid is used, and more preferably when less than 20% acetic acid is used, the formulation is still effective in straightening hair and also may be used even when the scalp or skin is scaly, scratched, or tender, without the need to apply protective creams. Thus, applicant considers formulations having from 8 to 30% alkanoic acid to be preferred, and formulations having from 9 to 20% alkanoic acid to be even more preferred. In one embodiment, the formulation is used to reduce or control frizziness that may arise with humidity. In that instance, an alkanoic acid concentration of 2 to 30% is preferred, more preferably 2 to 20%, and even more preferably 2 to 10%.

With this invention, alkaline agents are not used to perform a hair straightening function. The inventive hair straightening formulation is acidic, not alkaline. Before and/or after the formulation for straightening the hair is applied, shampoos, conditioners and various other hair care products may be used on the hair. Some shampoos, conditioners and/or styling gels may contain alkaline agents. Typically, however, the alkaline ingredients are present in small quantities, and many shampoos, conditioners, and styling aids have pH values in the range of 5.5 to 7.5. In fact, the pH values of typical hair products are often adjusted downward to about 4.5 to 5.5 in order to be "pH balanced," reflecting the lower pH of skin (4.5). The degree of alkalinity and/or amounts of alkaline agents in these products are not effective to perform a hair straightening function. An "effective amount" of an alkaline hair straightening as used herein means use of a sufficient amount of an alkali base, e.g., sodium hydroxide, potassium hydroxide, or lithium hydroxide, to cause a temporary or permanent straightening of the hair shaft. Typically, such an effective amount comprises use of about 1.8 to 4.0% w/w of the alkali base. Consequently, even when such auxiliary products are used, the method of straightening hair according to this invention does not include use of an effective amount of an alkali hair-straightening agent.

This invention applies a method of straightening hair with use of a low pH (less than 7 pH, typically less than 6 pH, and more preferably less than 5.5 pH). The invention teaches that a dilute solution of a weak, non-sulfur containing alkanoic acid (e.g., acetic acid in greater than 50% water) has the ability to disrupt salt and hydrogen bonds within keratin fibers of hair shafts. This teaching is contrary to all prior methods and chemical theories for modifying the configuration of human hair, which as described above have typically used sulfur-containing compounds and/or alkali agents. Typical mercaptan-based hair treatment solutions require a pH in excess of neutrality and normally exhibit a pH above 9.0.

As used herein, the term "alkanoic acid" refers to carboxylic acids with alkane, alkene, or similar substituents. Alkanoic acids have the following atomic grouping:

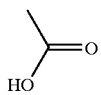

The preferred alkanoic acid is acetic acid ($CH_3COOH$). Acetic acid ($CH_3COOH$) is a non-polar solvent:

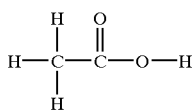

Acetic acid may be identified as glacial acetic acid (in pure form), and in water solution as ethanoic acid, ethylic acid, methanecarboxylic acid, pyroligeneous acid, and vinegar acid. Vinegar is a 5% aqueous solution of acetic acid.

However, other alkanoic acids are suitable for use in the inventive formulation. For example, propanoic acid is effective, and may be combined with use of acetic acid. Aqueous formulations containing 12% acid with 50/50 acetic and propanoic acids were found to be effective (Examples 11 and 12, below.) It has been found that a 15% lactic acid solution and a 20% maleic acid solution (aqueous solutions of lactic acid and maleic acid in water) were effective in hair straightening. Other suitable acids include, but are not limited to, methanoic acid, 2-methylbutanoic acid, 2-methylpropanoic acid, 2,2 dimethylpropanoic acid, decanoic acid, octanoic acid, hex-2-enoic acid, heptanoic acid, 6-methylheptanoic acid, 3-ethylpentanoic acid, 3-chloropentanoic acid, 2-hydroxypropanoic acid, 2-chloro4-hydroxyhexanoic acid, hexanedioic acid, octadecanoic acid, 4-oxopentanoic acid, and 6-hydroxy4-oxonanoic acid.

Advantageously, the inventive formulation contains at least 5% of the acetic acid, but not greater than 30%. A preferred formulation for hair straightening comprises use of about 10 to 20% acetic acid, more preferably about 10–12% acetic acid, diluted in greater than 50% water or other diluent. The effectiveness of the formulation per individual treatment will generally increase when the concentration of acid is increased above 20% up until a point; however, formulations having more than 20 to 30% alkanoic acid may irritate the skin, causing a burning sensation. Also, a formulation having 95% acetic acid in water is less effective than a formulation having 5% acetic acid in water. Thus, formulations having greater than 30% acetic acid will lose their effectiveness at a certain point, and 99% acetic acid is not effective. Thus, it is recommended that concentrations below 20% alkanoic acid be used. Also, formulations having less than about 10% acid are still effective and may be preferred for maintaining the straight condition of previously-treated hair. For example, for hair-straightening maintenance, a formulation having about 2 to 5% alkanoic acid is advantageous. However, to perform the hair straightening function itself, formulations having less than 10% alkanoic acid will take a longer period of time to be effective than formulations having more acid, and thus, repeated treatments and/or treatments for longer periods of time may be needed.

Advantageously, the alkanoic acid is a weak acid. The term "weak" acid is used to refer to acids which only feebly conduct electricity (low conductivity) and are only partially ionized in solution. For example, the electrical conductivity of acetic acid ($C_2H_3O_2H$), at a molarity of 0.1 is 4.67 reciprocal ohms (mho). This contrasts to the conductivity of strong acids which ionize completely in solution and have high conductivities ranging from 60 to 350 mho at the same molarity.

The term "diluent" as used herein refers to substances that may be used to dilute the alkanoic acids. Water is the preferred diluent. The formulations require use of greater than 1% water to be effective. Advantageously, greater than five percent water is used, and more preferably, greater than 50%, and even more preferably, greater than 80% water is used. Alcohols such as ethyl alcohol and isopropyl alcohol may be used at low concentrations (~5%) to enhance shaft penetration and reduce odor. High concentrations (~35% and greater) of alcohols are not suitable as they disrupt the effectiveness of the formulation.

The reactivity (effectiveness) of the inventive formulation can be modulated by the concentration of the solution and the temperature. When 0.01 mole of pure acetic acid is dissolved in a liter of water at room temperature, about 4% of the solute will be ionized by the time equilibrium is reached. However, this position of equilibrium will vary depending upon the temperature and concentration. For example, if 0.1 mol of pure acetic acid is added to a flask so that the final volume is 1 liter, only 1.3% of the acetic acid is ionized to cetate. The remaining 98.7% remains in solution. An increase in temperature will also shift the position of equilibrium in the direction of the process absorbing energy and make the acid more reactive with carboxylic amino acids.

It will be appreciated that auxiliary ingredients may be added to the formulations to mask the scent of the acid and/or perform other functions besides hair straightening, such as cleansing or conditioning. Also, gelling agents such as XANTURAL® gum or other known gelling agents may be used to create a desired consistency or viscosity to the formulation. Advantageously, such auxiliary components comprise less than 50% of the formulation, more preferably less than 30%, and even more preferably less than 20/% of the formulations. The auxiliary components added to the formulations may include hydrolyzed soy protein, safflower oil, aloe vera and other natural or synthetic moisturizers, glycerin, lactamide MEA, panthenol (Vitamin B), keratin amino acids, phytolipids, Shea butter or lanolin, mineral oil, petrolatum, laneth-15, PEG-40 Stearate, milk protein, methylparaben, papaya and other fruit extracts, chamomile, anti-oxidants such as vitamin E, gamma linolenic acid, babassu oil, evening primrose oil, lesquerella oil, jojoba oil, rose hips oil and other plant oils, sea kelp; sunscreen factors; styling gels and aerosols, witch hazel and other natural or synthetic setting agents; salicylic acid, quaternium 15, thymol, eucalyptol, methyl salicylate and other anti microbial agents, coal tar solutions, alcohols, and other compounds medicinal or cosmetic to hair and scalp; perfuming masks such as menthol, wintergreen oil, floral and other fragrances, caramel, artificial colorants, and other enhancers.

In application, the formulations can be applied to the hair and left in the hair, or they may be rinsed out, followed by cleansing and/or conditioning treatments. It is intended that the formulations will be repeatedly applied to obtain maximum results. For example, a formulation having a 10% concentration of alkanoic acid (aqueous) can be applied to the hair for about 30 minutes two to three times a week for several weeks to straighten kinky hair to a desired condition. The hair may be placed in rollers or pulled straight as the formulation is applied to provide mechanical assistance to the straightening function.

The hair straightening formulation can be administered in conjunction with other compositions and methods of treating and styling hair such as hair sprays, shampoos, conditioners, hot oil treatments, styling gels, heat curling, heat combing, chemical processing (e.g., dying, bleaching, alternative methods of chemical straightening and permanent waving, etc.). The formulations may be used in combination with hair conditioners such as hydrolyzed soy protein, safflower oil, aloe vera and other natural or synthetic moisturizers, glycerin, lactamide MEA, panthenol (Vitamin B), keratin amino acids, phytolipids, Shea butter or lanolin, mineral oil, petrolatum, laneth-15, PEG-40 Stearate, milk protein, methylparaben, papaya and other fruit extracts, chamomile, anti-oxidants such as vitamin E, methylsulfonylmethane, gamma linolenic acid, babassu oil, evening primrose oil, lesquerella oil, jojoba oil, rose hips oil and other plant oils, sea kelp; sunscreen factors; styling gels and aerosols, witch hazel and other natural or synthetic setting agents; salicylic acid, quaternium 15, thymol, eucalyptol, methyl salicylate and other anti microbial agents, coal tar solutions, and other compounds medicinal or cosmetic to hair and scalp; perfuming masks such as menthol, floral and other fragrances, caramel, artificial colorants, penetration enhancers such as alcohols and other enhancers.

Method of Applying the Formulations to Straighten the Hair. An exemplary method of straightening hair utilizes a 5% solution of acetic acid in warm-to-hot tap water (90°–105° F.) at a ratio of 20 parts tap water to 1 part 5% acetic acid (aq) which is freshly prepared in a basin or bowl. Higher concentrations of the alkanoic acid may be used depending on the results desired and hair type (e.g., kinky vs. curly hair). For hair that is difficult to straighten (such as African American hair) or hair that is very delicate or damaged (such as naturally blond and permed hair) adjustments may be made in the temperature and concentration of the method to maximize results or minimize harshness, keeping in mind that with dilution, a milder straightening and setting solution is formulated.

Effectiveness and reactivity may be enhanced by increasing the temperature of the water. The "position of equilibrium" of the agent will vary depending upon the temperature and concentration. An advantageous temperature is between 95°–105° F.

In addition to the preferred alkanoic acids (acetic or propanoic), pure acetic acid (glacial acid), or other pure alkanoic acid as identified above, and water will achieve the same results. One may wish to adjust the concentrations of the ingredients according to the type of hair being straightened, method of application, duration of exposure per treatment, and number of treatments anticipated before the desired hair curl relaxation is achieved. For example, different concentrations may be used for initial hair-straightening, hair-straightening maintenance, relaxation of curl, and reduction of frizziness of hair produced from humid weather. Also, different types of hair may require different concentrations of alkanoic acids, e.g., African American kinky hair may in some instances require concentrations of alkanoic acids at about 10% or higher, while it is possible that Caucasian curly hair can be straightened using a series of leave-in rinses at concentrations as low as 0.25% alkanoic acid. Additionally, those who wish simply reduction in frizziness or hair-straightening maintenance may require a concentration between about 0.25% and 9.75% alkanoic acid. Furthermore, a lesser concentration may be needed for leave-in rinse as compared with a rinse-out gel.

Various methods of applying the formulation to the hair are contemplated. According to one aspect of the invention, the formulation is provided in the form of a leave-in rinse. The rinse is applied by submerging clean, damp hair into a freshly-made bath of the solution for approximately 15 seconds to 60 seconds. The hair is then towel dried, optionally treated with a styling gel, and combed straight or smoothed back or around the head in a straight configuration, and air-dried or dried by heat. Once dry, the hair may be curled or smoothed by heat appliances (heat rollers, wands, blow dry brushes, heat combs, etc.) into the desired style. The rinsing procedure may be repeated daily, weekly or periodically until the desired degree of straightness is achieved. The rate of response to the treatments will depend upon the amount of curl, the porosity of the hair from previous chemical treatments, and the natural thickness of the cuticle. The more porous the cuticle the more responsive the hair to the alkanoic acid rinses. Hair that does not straighten when wet can be pulled mechanically or assisted with heat rollers or gels after treatment.

Continuous and unmonitored immersion may in some cases tend to weaken the hair shaft. It is recommended that continuous use be accompanied by the addition of conditioners, hot oil/cream treatments, and the trimming of dried ends, as required, to maintain shine and feel attributes. The distal ends of previously dyed, permanently waved or straightened will respond more rapidly to the alkanoic acid rinses hair, due to their increased porosity (the result of more frequent exposure to chemicals and the sun, etc.). A user may desire to trim or provide extra conditioning to previously-treated hair.

The following examples will serve to further typify the nature of the invention, but should not be construed as a limitation on the scope thereof, which is defined solely by the appended claims.

EXAMPLE 1

| Ingredients | Weight % |
| --- | --- |
| 10% acetic acid (aqueous) | 97.9 |
| XANTURAL ® gum powder (gelling agent) | 1.7 |
| Fragrance | 0.4 |
| | 100 |

This example uses about 88.1% water and 9.8% acetic acid. The ingredients are combined in the form of a gel. The product may also be formulated with glacial acetic acid (pure) and deionized water to equal 10% acetic acid. This formulation is referred to as a "wash out" composition as it is adapted to be left in the hair for a period of time and then rinsed out.

According to one method of application, the formulation is applied to wet, clean hair and combed through. The hair may be pulled straight with curlers, clips or by tying or braiding the hair. The formulation is left on the hair for from 30 minutes to 12 hours, allowing the formulation to dry on the hair if necessary, depending on degree of straightness desired and original curl in hair. The gel is then rinsed out and the hair optionally washed with shampoo. The hair is optionally conditioned with hair conditioning product(s) and styled, preferably with a heat appliance, such as heat curlers, heat curling or flat wand. This process may be repeated, as above, until the desired curl relaxation is achieved. The hair may be treated periodically with oil or mineral supplement conditioners to prevent dryness.

EXAMPLE 2

| Ingredients | Weight % |
| --- | --- |
| Deionized water | 63.40 |
| 10% Acetic Acid (aqueous) | 20.00 |
| XANTURAL ® gum (gelling agent) | 1.30 |
| Methylsulfonyl Methane (hair conditioner) | 15.00 |
| Fragrance | 0.20 |
| Methyl Paraben (preservative) | 0.05 |
| Propyl Paraben (preservative) | 0.05 |
| | 100 |

Thus, this formulation in combination contains a total concentration of acetic acid of about 2% w/w. The formulation is referred to as a "leave in" formulation as it is intended to be applied to the hair in gel form without subsequent rinsing.

According to one method of application, the formulation is applied to wet, clean hair and combed through. The hair is set with curlers or other styling aids and blown dry. The formulation is not rinsed out. The hair will gradually straighten with repeated use.

The formulation also may be applied to dry hair as a spray formulation to control frizz and as a setting agent between shampoos.

EXAMPLE 3

| Ingredients | Weight % |
| --- | --- |
| Deionized water | 77.15 |
| 10% Acetic Acid (aqueous) | 6.25 |
| XANTURAL ® gum (gelling agent) | 1.30 |
| Methylsulfonyl Methane (hair conditioner) | 15.00 |
| Fragrance | 0.20 |
| Methyl Paraben (preservative) | 0.05 |
| Propyl Paraben (preservative) | 0.05 |
| | 100.00 |

Thus, this formulation in combination contains a total concentration of acetic acid of about 0.6% w/w. The product may also be formulated with glacial acetic acid (pure) and deionized water to equal a 10% acetic acid ingredient. This formulation is designed to gradually straighten moderately curly hair, reduce frizz, and prevent curling of straightened hair (e.g., as maintenance). According to one method of application, the formulation is applied to wet, clean hair and combed through. The hair may be allowed to dry naturally, set with curlers or other styling aids, or blown dry. The formulation is not rinsed out. The hair will gradually straighten with repeated use or maintain straightness achieved with previous treatment, particularly during humid weather. The formulation also may be applied to dry hair as a spray formulation to control frizz and as a setting agent between shampoos.

EXAMPLE 4

The formulation of Example 1 was prepared as follows. 24.475 kg. of 10% acetic acid (aqueous) was weighed and transferred into a colloid mill circulation tank. 100 gms. of fragrance were then added to the mixing tank while agitating slowly. 425 gms. of XANTURAL® 11K gum powder were added to the hopper of the colloid mill circulation while the liquid was circulating to ensure good wetting of the powder. After all the gum power was added, the solution was circulated for 15–30 minutes or until the solution was uniform. A sample was taken from the tank and the viscosity measured with a Brookfield viscometer with an appropriate spindle. The pH and density were measured, and the solution transferred to the filler feed tank. The result is a bath of about 25 kg (approx. 55 lbs) of a formulation having the constituents as set forth above in Example 1.

EXAMPLE 5

An African American female subject washed and towel dried her hair. A formulation as in Example 1, above, but with a 15% acetic acid solution (with a reduction in water to make up the difference) was applied to a section of the subject's hair, and two swatches were separated. One swatch of hair was wound on a curler; another left without tension. After ten minutes, the swatches were compared and the curled swatch was observed to be straighter. Both swatches were then wound on curlers and left for 15 additional minutes. The hair was then rinsed in warm water, washed with shampoo, and treated with a washout conditioner. The hair swatches were then dried and curled using household electric curlers. Both swatches were straight in texture. The formulation was then applied to the rest of the subject's hair, and left for 15 minutes, as curlers were used to pull the hair straight. The result was that the subject's hair was observed to be substantially straighter.

EXAMPLE 6

A mulatto female subject having kinky hair washed her hair, and a 15% acetic acid gel (as in Example 5) was applied to her hair as wet. Half of the subject's hair was set on large rollers, and the subject sat with her hair under a medium-heat hair dryer for 20 minutes. The remaining half of the subject's hair was worked by hand-pulling and continuous combing, then twisted into braids. After total exposure time of 1 hour and 5 minutes, the hair was rinsed, shampooed and conditioned. The hair was reset and dried under hood. The kinky texture was replaced by ½ inch to 2-inch waves over all treated areas.

EXAMPLE 7

Figure 1B:
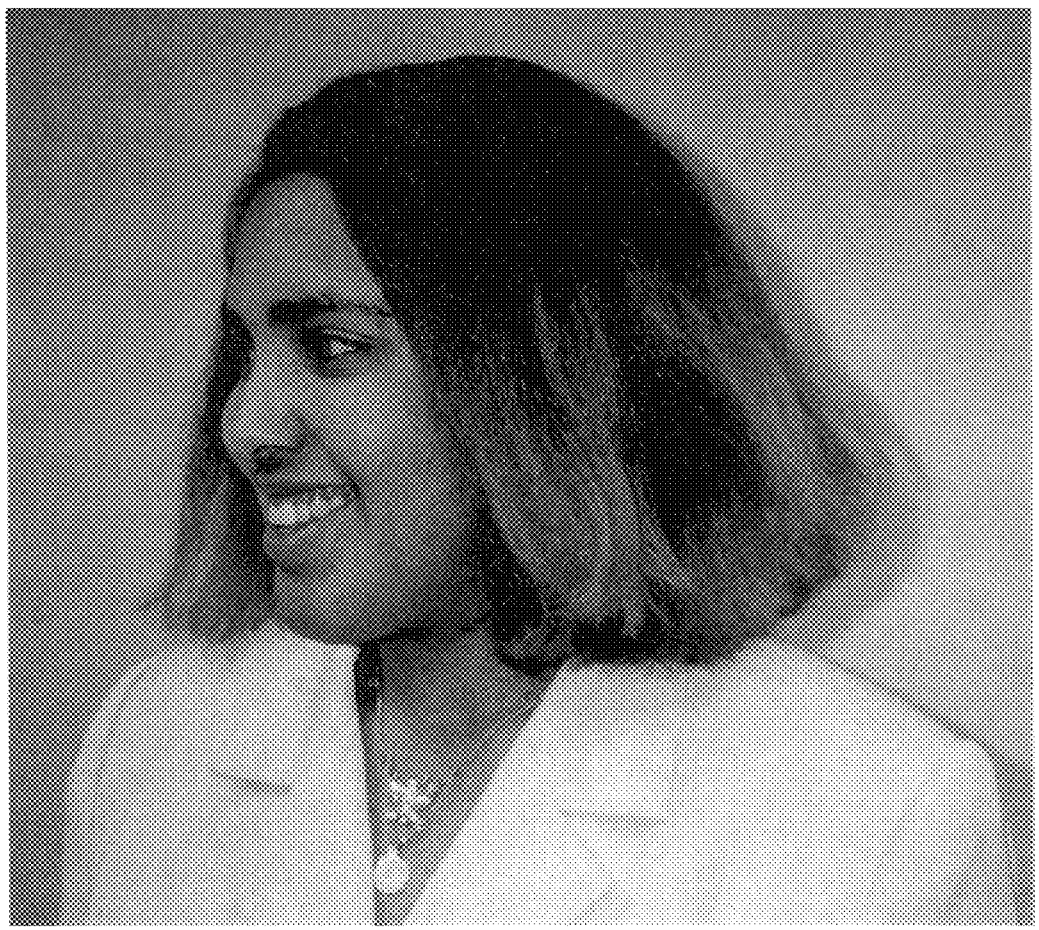
Figure 2A:
FIGS. 2A and 2B are photographs showing the condition of a subject's hair before and after treatment, respectively, with one embodiment of the inventive formulations using 18% acetic acid and greater than 50% water as a diluent.
Figure 2B:

Two mulatto female subjects having kinky hair submitted to treatment with an 18% acetic acid gel formulation. This formulation contained about 50.3% water, 18% acetic acid, 1.7% XANTURAL® gum, and 30% of a fragrance/odor masker. The appearance of the hair pre-treatment is shown in FIGS. 1A and 2A, respectively. The subjects' hair was washed, and the wet, clean hair was treated with the formulation. The treated hair was set in curlers for one hour, and the hair was then blown dry using a hair brush. The result was that the subjects' hair was observed to be substantially straighter as shown in FIGS. 1B and 2B.

EXAMPLE 8

Figure 3A:
FIGS. 3A and 3B are photographs showing the condition of a subject's hair before and after treatment, respectively, with one embodiment of the inventive formulations using 10% acetic acid and greater than 80% water as a diluent.
Figure 3B:

A Caucasian (Eastern European) subject having curly hair as shown in FIG. 3A was treated with a two minute bath of diluted 10% acetic acid applied to the hair. The subject placed dry hair in the bath consisting of 10% acetic acid (aqueous) and 1.5 gallons of water. Hair was left in the bath for two minutes then towel-dried. Hair was set in large curlers and the subject was placed under a bonnet hair dryer until the hair was dry. This method resulted in a hair style that was full and smooth. Results are shown in FIG. 3B.

EXAMPLE 9

Figure 4A:
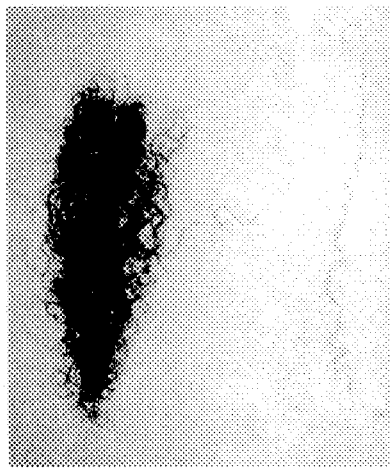
FIGS. 4A and 4B are photographs showing the condition of a subject's hair before treatment (FIG. 4A) and after five treatments (FIG. 4B), with one embodiment of the inventive formulations using 5% acetic acid.
Figure 4B:
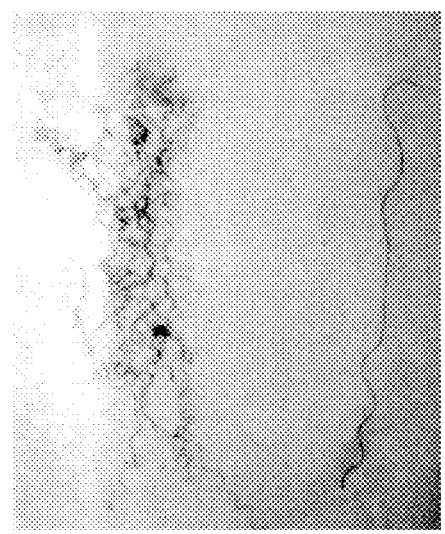

A lock of hair from a middle-aged African American woman which had never been treated with permanent waving or straightening chemicals or dyes was given five treatments of a formulation having a 5% acetic acid solution in a ⅕ gallon bath of water. The lock was rinsed her hair two to three times weekly, and after five treatments, the desired results were achieved. The hair had begun to lose its curl on its own after the first three treatments, and mechanical assistance was applied thereafter. This was done with a thick styling gel (4th treatment) and with scotch tape (5th treatment). The "before" and "after" results of this test are shown in FIGS. 4A and 4B.

EXAMPLE 10

Figure 5A:
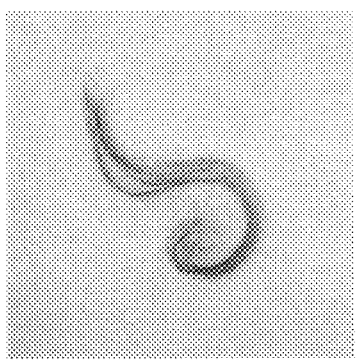
FIGS. 5A, 5B, 5C are swatches of hair taken from a subject before treatment
Figure 5B:
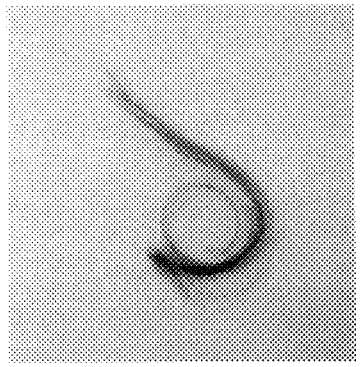
Figure 5C:
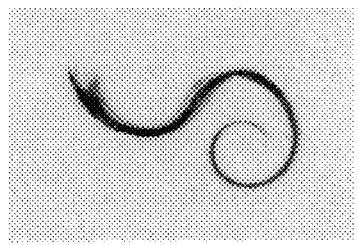
Figure 6A:
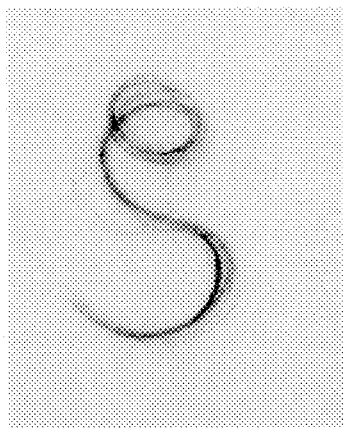
FIGS. 6A, 6B, and 6C are the same swatches after receiving a single fifteen-minute treatment with formulations containing glacial acetic acid and 1%, 5%, and 95% water, respectively.
Figure 6B:
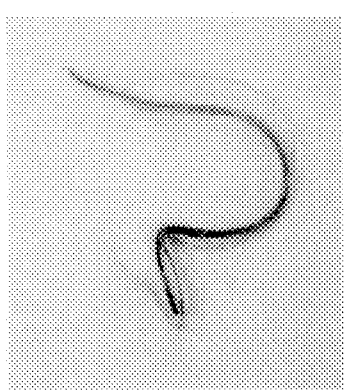
Figure 6C:
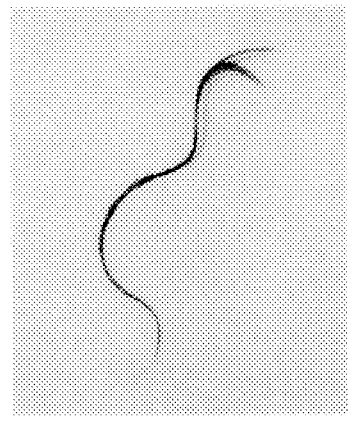

Three separate tests were conducted with different percentages of water. In particular, tests were conducted to show the results obtained from using acetic acid in 1% water (~99% acetic acid), 5% water (~95% acetic acid), and 95% water (~5% acetic acid). For these tests, identical locks of hair were cut from the same Caucasian female and photographed. The swatches before treatment are shown in FIGS. 5A, 5B, and 5C. Three solutions of water and acetic acid were prepared (having 1%, 5% and 95% water). The locks were submerged for 15 minutes in the separate solutions, e.g., one lock for each solution. Each lock was then lifted from its solution, permitted to dry, and photographed. The results are shown in FIGS. 6A, 6B, and 6C.

As can be seen, a greater hair straightening effect was achieved with 95% water as compared with 5% water. The 1% water solution did not produce any apparent hair straightening effect for this single treatment (FIG. 6A). It was determined that the hair-straightening effect was greater for the 95% water solution as compared with the 5% water solution in this instance.

EXAMPLE 11

An African American (mulatto) subject provided hair swatches from the right and left side of the head. The swatch from the right side received a formulation having an equal mixture of 12% acetic acid/12% propionic acid for ten minutes. The left side was treated with 12% propionic acid only for ten minutes. Hair swatches were then rinsed and shampooed. Swatches were then blow-dried and set with electric heat curlers. Both formulations resulted in the elimination of tight curls, leaving hair wavy.

EXAMPLE 12

A Caucasian subject having curly, red hair was treated with application to the hair of a formulation having a 12%, 50/50 aqueous mixture of propionic and acetic acid. The formulation was applied to a frontal swatch of hair for ten minutes. No curlers were necessary as hair combed straight. Hair was then rinsed, shampooed, blow-dried, and heat-curled on household rollers. Result was a loose wave.

EXAMPLE 13

A Caucasian subject having curly hair was treated with application of a 9.75% acetic acid gel to the hair. The hair was combed into a bun, covered with a shower cap, and left overnight. Hair was washed and dried the following morning. Hair was significantly straighter. Hair was then set on heat rollers. Result was a straight configuration with slight wave properties in response to roller setting.

EXAMPLE 14

A Caucasian subject with hair previously straightened by weekly baths of 5% acetic acid used the 2% acetic acid gel formulation (as in Example 3 above) after each hair washing. Result was improved texture (softness and shine) and maintenance of a straight shaft and straight new growth.

EXAMPLE 15

The hair of a Caucasian female with chemically dyed (brown), naturally curly, gray hair, was bathed in a 5% acetic acid solution/1.5 gallon water bath (equally a 0.25% w/w concentration of acetic acid) for 20 seconds and allowed to dry as a leave-on rinse bi-weekly for a period of 12 weeks for a total of 24 treatments. After two applications her hair demonstrated improved shine and manageability after heat setting with rollers. After four applications, heat-set curls remained in place at humidity levels of 80%. After six applications, her hair, formerly "frizzie" after washing, dried straight and heat-set curls remained in place at 100% humidity levels. After twelve applications, the subject's hair was examined and compared to samples taken prior to the series of treatments. The treated shaft was visibly straighter. Acetic acid baths continued at a lower acetic acid concentration of 80:1 through week 12 and bi-weekly hot oil treatments were added. Reexamination of sample specimens during week 13 indicated that the shafs had sufficient moisture and shine without compromising straightness or heat curl retention. The subject discontinued acetic bath treatments after 12 weeks and indicated that no more were necessary as her hair remained easy to style, without frizziness on humid days despite frequent shampooing.

EXAMPLE 16

A Caucasian male with short, dark blond, naturally curly hair, was treated with one submersion in a 0.25% acetic acid bath. The hair was towel-dried and the rinse allowed to air dry on the hair. Observation when dry indicated that approximately 70% of the natural curl had been eliminated. The subject did not seek re-treatment indicating he was happy with the results. Eight weeks later, the subject reported that the hair was still surprisingly "manageable."

EXAMPLE 17

Two sets of severed locks of chemically-straightened hair (exhibiting some reversion to natural curl) from an African-American female subject were submerged for 15 seconds in a 5% acetic acid aqueous solution and allowed to remain on the hair for 30 minutes. A similar set of locks was rinsed in pure tap water as a control. Both sets of locks were then shampooed, conditioned, rinsed with water, combed out and allowed to air dry. The treated locks exhibited less reversion and curling than did the control locks.

Mechanism of Action. The formulations and methods described herein are believed to change the charge on the carboxylic amino acids within keratin causing both the loss of hydrogen and ionic bonding properties and secondary to these events, the disassociation of some of the disulfide bridges from the helix structure itself which are a principle force in the maintenance of natural curl. With the loss of hydrogen and ionic bonding, the keratin is partially denatured. The shaft becomes less sensitive to external moisture and more sensitive to heat-induced curling. With the partial loss of secondary and tertiary structure involving disulfide bridges, naturally curly hair loses its wavyness.

While not wishing to be bound by any one theory, it is believed that the present formulations are capable altering the secondary structure of keratin's polypeptide chain by reacting with the carboxylic acids and, in turn, the amine bases of this protein. In this reaction, the amino acids, glutamic acid and aspartic acid, are protonated with their electron charge changing from negative to neutral/positive. This reaction is believed to result in the following denaturing events:

1. Protonation of glutamic acid and aspartic acid causes these amino acids to turn inward on themselves or "inside out", changing at these locations the hydrogen bonding distances and strength.
2. Salt bridges are also cleaved with the change in aspartic and glutamic acid electron charge. As is known, these negatively-charged amino acids form ionic bonds, also know as salt-bridges, with arginine and lysine which are positively charged. When the former lose their charge the ionic bonds cleave and the keratin is further denatured.
3. Disulfide bonds "let go", it is thought, as protonation deconfigures the protein's secondary structure. These bonds are still in place but no longer anchored on the chain.

Once a percentage of the ionic, hydrogen and cysteine bonds are cleaved by repeated rinsing with the weak alkanoic acid aqueous solutions, naturally-curly hair will remain straight with improved response to heat curling and reduced response to humidity.

I claim:

1. A hair-straightening formulation having a pH greater than about 2.4 consisting essentially of:
   (i) about 8% to about 30% by weight of at least one alkanoic acid;
   (ii) an acceptable diluent; and
   (iii) less than about 30% of at least one auxiliary component selected from a fragrance, an odor masker, conditioner, gelling agent and penetration enhancer.

2. The formulation of claim 1 said diluent comprising water and fragrance and at least one other auxiliary component.

3. The formulation of claim 1 said diluent comprising at least 50% water by weight, and at least one other auxiliary component that is not fragrance.

4. The formulation of claim 1 in which the alkanoic acid is selected from the group consisting of acetic, methanoic, ethanoic, 2-methylbutanoic, propanoic, 2-methylpropanoic, 2,2 dimethylpropanoic, decanoic, octanoic, 2-hexenoic, heptanoic, 6-methylheptanoic, 3-ethylpentanoic, 3-chloropentanoic, 2-hydroxypropanoic, 2-chloro-4-hydroxyhexanoic, hexanedioic, octadecanoic, 4-oxopentanoic, and 6-hydroxy-4-oxonanoic acids.

5. A hair-straightening formulation having a pH greater than about 2.4 consisting essentially of about 8% to about 30% by weight of at least one alkanoic acid diluted in at least 50% water by weight; and less than 30% by weight of at least one auxiliary component selected from a fragrance, odor masker, conditioner, penetration enhancer and gelling agent.

6. The formulation of claim 5 having a pH value of less than 7.0 effective for straightening hair.

7. A hair-straightening formulation having a pH greater than about 2.4 consisting essentially of approximately 8% to approximately 70% of at least one alkanoic acid diluted in acceptable diluent comprising at least five percent water by weight.

8. The hair-straightening formulatin of claim 7 having a pH of less than 7.0.

9. A formulation for hair-straightening maintenance, relaxation of curl, and reduction of frizziness of hair having a pH greater than about 2.4 consisting essentially of approximately 8% to approximately 70% of at least one alkanoic acid diluted in an acceptable diluent comprising at least five percent water by weight.

10. The formulation according to claim 5 having a pH of 5.5 or lower.

* * * * *